United States Patent [19]

Green

[11] Patent Number: 4,665,223

[45] Date of Patent: May 12, 1987

[54] PROCESS FOR THE PRODUCTION OF 1-ALKOXYALKYL ESTERS

[75] Inventor: Michael J. Green, Hull, England

[73] Assignee: BP Chemicals Limited, London, England

[21] Appl. No.: 691,680

[22] Filed: Jan. 15, 1985

[30] Foreign Application Priority Data

Jan. 24, 1984 [GB] United Kingdom ............... 8401833

[51] Int. Cl.$^4$ .................... C07C 67/29; C07C 69/003
[52] U.S. Cl. ................................ 560/263; 260/410.5; 260/410.6; 560/8; 560/106; 560/112; 560/193; 560/198; 560/221; 560/224; 560/254; 560/262; 560/265; 560/234; 568/484
[58] Field of Search ............... 560/262, 263, 193, 224, 560/221, 254, 198, 112, 106, 8; 260/410.6, 410.5

[56] References Cited

U.S. PATENT DOCUMENTS

| | | | |
|---|---|---|---|
| 1,791,301 | 2/1931 | Davidson | 560/263 |
| 2,446,171 | 8/1948 | Croxall et al. | 560/263 |
| 2,723,287 | 11/1955 | Copenhaver | 560/263 |
| 2,823,226 | 2/1958 | Tsukamoto et al. | 560/263 |
| 4,419,280 | 12/1983 | Boden | 252/522 R |

*Primary Examiner*—Vivian Garner
*Attorney, Agent, or Firm*—Brooks Haidt Haffner & Delahunty

[57] ABSTRACT

A process for the production of 1-alkoxyalkyl esters comprises reacting an unsaturated ester with an alcohol in the presence of a Lewis base containing catalyst. The Lewis base containing catalyst is preferably (i) an amidine, or (ii) a Lewis base and an epoxide or (iii) a trivalent organophosphorus compound in the presence of an activated alkene or alkyne. The process can be used to prepare, for example, 1-methoxyethyl acetate from vinyl acetate and methanol under mild conditions.

18 Claims, No Drawings

PROCESS FOR THE PRODUCTION OF 1-ALKOXYALKYL ESTERS

The present invention relates to a process for the production of 1-alkoxyalkyl esters from an organic alcohol and an unsaturated ester in the presence of a catalyst containing a Lewis base.

1-alkoxyalkyl esters which have the general formula

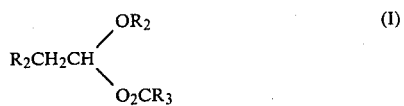

have previously been prepared by a stoichiometric reaction between a 1-chlorosubstituted ether and a sodium salt of a carboxylic acid (J. Amer. Chem. Soc. 63 2201 (1941)).

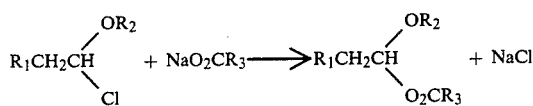

and also via the addition of a carboxylic acid to an unsaturated ether (Chem. Abs. 48 579)

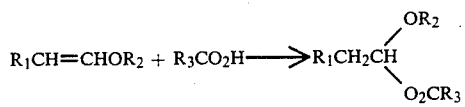

but there is no precedent for the formation of this class of compounds from an organic alcohol and an unsaturated ester.

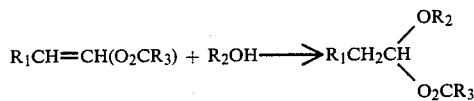

It has now been found that 1-alkoxyalkyl esters can be prepared from an unsaturated ester and an organic alcohol in the presence of a catalyst which contains either wholly or in part a Lewis base.

Accordingly, the present invention provides a process for the production of 1-alkoxyalkyl esters which process comprises reacting an unsaturated ester with an alcohol in the presence of a Lewis base containing catalyst.

The unsaturated ester used as a reactant is one of a class of compounds having the formula

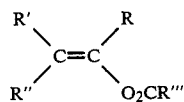

wherein $R'''$ is a saturated or unsaturated alkyl, aryl or alkaryl hydrocarbyl radical and $R, R'$ and $R''$ are independently hydrogen atoms, an $-O_2CR'''$ group or a saturated or unsaturated alkyl, aryl or alkaryl hydrocarbyl radical. The unsaturated ester is suitably an ester of acetic acid, propionic acid, acrylic acid, methacrylic acid, maleic acid or substituted derivatives thereof. Preferred esters are vinyl acetate and vinyl propionate.

The alcohol used may be either an aliphatic or aromatic alcohol or a substituted derivative thereof. Unsaturated alcohols, for example allyl alcohol or polyols such as ethylene glycol, may also be used. Preferred alcohols are methanol, ethanol, propanol, phenol ethylene glycol and glycerol.

The process as described herein is particularly useful when the unsaturated ester is vinyl acetate and the alcohol is either methanol or ethanol since the process then uses feedstocks which themselves can be exclusively derived from carbon monoxide and hydrogen. It is thought that, in the future, carbon monoxide and hydrogen will be an alternative to ethylene as a major raw material for the chemical industry.

The production of the 1-alkoxyalkyl ester is catalysed by a Lewis base containing catalyst. The term Lewis base is one familiar to the skilled man and is defined, for example, on page 614 of "The Condensed Chemical Dictionary (10th Edition)" published by Van Nostrand Reinhold Company. Examples of Lewis bases include amines, phosphines, arsines and stibines. Suitably, the Lewis base used in the present invention is a strong base or is capable of generating a strong base in the presence of other catalyst components. Hence, the Lewis base containing catalysts used in the present invention are themselves strongly basic.

Preferably, the Lewis base containing catalyst belongs to one or more of the following three classes of compounds;
 (1) an amidine,
 (2) a Lewis base in the presence of an epoxide, and
 (3) a trivalent organophosphorus compound in the presence of an activated alkene or alkyne.

By the term amidine is meant a compound containing the grouping

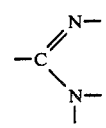

Conveniently the free valencies on the nitrogen atom are attached to carbon atoms or hydrogen and the free valency on the carbon to another carbon or nitrogen atoms. In the last mentioned case the structure comprises a guanidine grouping.

A preferred class of amidines is the cyclic amidines. Cyclic amidines are defined as those amidines wherein at least one of the nitrogen atoms is part of an alicyclic or heterocyclic substituted or unsubstituted hydrocarbyl ring. In the case where the amidine is a guanidine then any two of the three nitrogen atoms may be in the same or different rings. Those nitrogen atoms which are not part of any such ring may form part of a substituted or unsubstituted hydrocarbyl group.

A preferred class of cyclic amidines is that in which the amidine group can form part of a fused ring system containing 6 and 5 membered rings or 6 and 7 membered rings or two six membered rings, as for example in 1,5-diazabicyclo[4.3.0]non-5-ene which has the formula

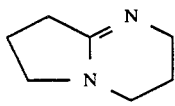

or 1,8-diazabicyclo[5.4.0]undec-7-ene of the formula

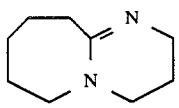

or 1,5,7-triazabicyclo[4.4.0]dec-5-ene of formula

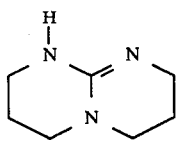

Where the catalyst comprises a Lewis base and an epoxide the epoxide which is used in the presence of the Lewis base is preferably a lower alkylene oxide such as ethylene oxide, propylene oxide or butylene oxide. The ratio of Lewis base to epoxide suitably lies in the range 1:1 to 1:5. In such cases the Lewis base is preferably an amidine or an alkylamine, e.g., triethylamine.

Where the catalyst is an organophosphorus containing compound/activated alkene/alkyne catalyst, it suitably comprises the following parts (i) an organophosphorus containing compound in which the phosphorus is trivalent, and (ii) a compound containing both
  (a) a double or triple bond, and
  (b) an electron withdrawing group
the latter said compound being reactable in the Michael reaction.

The organophosphorus-containing compound can suitably be a mono-, di- or trialkyl phosphine in which each of the alkyl groups is a $C_1$ to $C_{10}$ alkyl group or a mono-, di or triaryl phosphate such as triphenylphosphine and can contain more than one phosphorus atom, e.g., $Ph_2PCH_2CH_2PPh_2$.

The compound (ii) containing the double or triple bond and electron withdrawing group can be of the formula

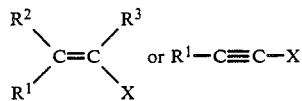

where X is an electron withdrawing group, for example —COOR, —COR, CHO, $CONH_2$, $CON(R)_2$ or CN, where R is an alkyl or aryl group, and where $R^1$, $R^2$ and $R^3$ are monovalent hydrocarbyl groups or hydrogen.

The molar proportions of the two components of the catalyst system are such as to provide from 10:1 to 1:10, preferably 2:1 to 1:2 atoms of phosphorus per double or triple bond.

Conveniently the catalyst system comprises a solvent in which both components are dissolved. The solvent is suitably an aliphatic alcohol and is preferably selected from the following alcohols, methanol, ethanol, propa- nol and butanol. The solvent of course can be one of the reactants.

The catalyst system can be prepared by mixing the two components in the presence of the solvent or one or more of the reactants.

For any of the three classes of catalyst, the preferred catalyst concentrations are in the range 0.1 to 2% by weight of the reaction mixture.

The Lewis base containing catalyst may be supported on an inert solid to render the catalyst insoluble in the reaction mixture. Such heterogeneous Lewis base containing catalysts are more easily separated from the reaction mixture at the end of the reaction than equivalent soluble (homogeneous) versions.

The amidine or guanidines catalysts described above may be supported by chemically or physically bonding the molecule to an inert solid. This can be achieved, for example, by bonding the surface atoms of the solid to one or more of the free valences of the amidine or guanidine group either directly or through an intermediate hydrocarbyl radical. In the case of cyclic amidines or guanidines the hydrocarbyl radical may constitute part of the ring structure of the molecule.

As an alternative to a supported amidine or guanidine catalyst, a supported Lewis base/epoxide catalyst can be used. In such catalysts, it is possible either (i) to support the Lewis base on the inert solid and have the epoxide component present in solution with the reactants.

or (ii) to support the epoxide on the inert solid and have the Lewis base component present in solution with the reactants.

The epoxide component, if present in solution is suitably a lower alkylene oxide for example ethylene oxide, propylene oxide and butylene oxide. If the epoxide is supported on the inert solid it also may be bonded to the solid via one or more of the groups attached to the epoxide moiety. However, if the inert solid is an organic resin it is possible to prepare the epoxy modified resin directly by polymerising epoxy functionalised monomers.

The trivalent organophosphorus compound/activated alkene or alkyne catalyst can also be used in a heterogeneous form. In this case either of the two components may be bound to the inert solid with the other component present in solution.

The inert solid may be either organic, such as a resin or a polymer, e.g. polystyrene, a polystyrene/divinylbenzene copolymer, a polyacrylate, polypropylene and the like, or inorganic such as a silica, clay, diatomaceous earth, zeolite, alumina or aluminosilicate. Preferred supports are polystyrene and its copolymers with divinylbenzene, copolymers of glycidyl methacrylate and ethylene glycol dimethacrylate and the like.

Examples of the supported strong base catalysts are TBD supported on polystyrene or polystyrene/divinylbenzene copolymer, amberlite IRA-93, Amberlyst IS and Duolite A375.

The Lewis base containing catalyst is suitably present on the soid in amounts corresponding to between 0.1 and 10 moles of catalyst per gram of solid.

It is clearly important that the solid is not degraded under the reaction conditions. Hence, by the term inert solid is meant a solid which does not undergo physical or chemical degradation during the reaction or subsequent processing. Since the reaction conditions may vary depending upon the nature of the reactants, reaction temperature, reaction time and the nature of any sovent used, the choice of inert solid will therefore reflect the particular needs and constraints of the process to be operated.

The reaction can be carried out over a wide range of temperatures but is preferably carried out at a low temperature in the range $-78°$ C. to $25°$ C. Low temperatures are preferred as under such conditions the yield of 1-alkoxyalkyl ester is increased and the yields of side products are decreased. When vinyl acetate and methanol ae used as reactants the 1-alkoxyalkyl ester produced is 1-methoxyethyl acetate and the major side products are methyl acetate and acetaldehyde.

The molar ratio of alcohol to unsaturated ester is suitably in the range 1:5 to 5:1.

The process can be operated either batchwise or continuously.

The invention is now illustrated by the following Examples.

EXAMPLE 1

A Fischer-Porter tube was charged with 6.5 g of methanol and 0.25 g of 1,8-diazabicyclo[5.4.0]undec-7-ene (DBU) and cooled to $-78°$ C. in a cardice (solid carbon dioxide)/acetone bath. 17.5 g of vinyl acetate was added dropwise and the resulting solution allowed to warm slowly to room temperature. Analysis of the liquid product by gas chromatography showed an 87% conversion of vinyl acetate with a 29.7% selectivity to 1-methoxyethyl acetate. The major side products were acetaldehyde and methyl acetate.

EXAMPLE 2

Example 1 was repeated except that the reaction tube was removed from the cardice/acetone bath immediately after the addition of vinyl acetate and allowed to warm quickly to room temperature. Analysis of the liquid product showed a 100% conversion of vinyl acetate with a 24.8% selectivity to 1-methoxyethyl acetate. This example shows that warming up the reaction mixture quickly from $-78°$ C. causes a decrease in selectivity to 1-methoxyethyl acetate.

EXAMPLE 3

Example 2 was repeated except that 0.25 g of tetramethyl-t-amyl guanidine was used as catalyst in place of DBU. Analysis of the liquid product showed a 100% vinyl acetate conversion and a 22.3% selectivity to 1-methoxyethyl acetate. This example shows that a guanidine may be used as catalyst.

EXAMPLE 4

Example 2 was repeated except that the DBU catalyst was replaced by 0.25 g of 1,5-diazabicyclo[4.3.0]-non-5-ene (DBN). A 70% vinyl acetate conversion was obtained with a 15% selectivity to 1-methoxyethyl acetate.

EXAMPLE 5

Example 2 was repeated except that the DBU catalyst was replaced by 0.5 g of triazabicyclo[4.4.0]dec-5-ene (TBD). A 70% vinyl acetate conversion was obtained with a 14.8% selectivity to 1-methoxyethyl acetate.

EXAMPLE 6

Example 2 was repeated except that 0.1 g of DBU was used. Analysis of the liquid product showed an 81.6% conversion of vinyl acetate with a 19.5% selectivity to 1-methoxyethyl acetate.

EXAMPLE 7

This example shows that a catalyst which comprises a Lewis base and an epoxide can be used to prepare 1-alkoxyalkyl esters from an unsaturated ester and an alcohol.

A Fischer-Porter tube was charged with 6.5 g of methanol, 0.2 g of triethylamine and 0.36 g of propylene oxide and then pressurised to 50 psi with nitrogen. The tube was heated to $100°$ C., cooled to room temperature and depressurised. Once the tube had been depressurised, it was further cooled to $-78°$ C. and 17.5 g of vinyl acetate was slowly added. The tube was removed from the cardice/acetone bath and allowed to warm quickly to room temperature. Subsequent analysis of the liquid product showed a 74% conversion of vinyl acetate with a 17.8% selectivity to 1-methoxyethyl acetate.

EXAMPLE 8

Example 7 was repeated in the absence of propylene oxide. Analysis of the liquid product showed that no 1-methoxyethyl acetate had been produced. Example 8 does not constitute part of the invention as described herein but shows that an epoxide is an essential part of the catalyst if the Lewis base used is not an amidine.

EXAMPLE 9

Example 7 was repeated except that 0.33 g of tributylphosphine was used in place of triethylamine and 0.49 g of ethyl acrylate used in place of propylene oxide. A 61% conversion of vinyl acetate was obtained with a 13.2% selectivity to 1-methoxyethyl acetate. This example shows that a phosphine and an activated olefin can together form an active catalyst for this reaction.

EXAMPLE 10

A Fischer-Porter tube was charged with 6.5 g of methanol and 0.25 g of TBD and cooled to $0°$ C. Vinyl acetate (17.5 g) was slowly added and the resulting solution allowed to warm to room temperature. Analysis of the liquid product showed a 50% conversion of vinyl acetate with an 8% selectivity to 1-methoxyethyl acetate.

EXAMPLE 11

Example 10 was repeated at room temperature. Analysis of the liquid product showed a 47% conversion of vinyl acetate with a 4% selectivity to 1-methoxyethyl acetate.

EXAMPLE 12

Example 5 was repeated in the presence of 0.25 g of TBD with the methanol replaced by 8.3 g of ethanol. A 26% conversion of vinyl acetate was obtained with a 22.5% selectivity to 1-ethoxyethyl acetate. This example shows that alcohols other than methanol can be used as feed.

I claim:

1. A process for production of 1-alkoxyalkyl esters characterised in that the process comprises reacting an unsaturated ester of the formula

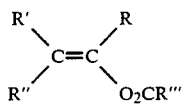

wherein R is hydrogen, R' and R" are independently hydrogen, an —O₂CR'" group, alkyl or an aryl hydrocarbyl radical and R'" is alkyl or an aryl hydrocarbyl group with an alcohol in the presence of an effective amount of a Lewis base containing catalyst, said Lewis base containing catalyst comprising one or more of the following:
(1) an amidine
(2) a Lewis base selected from the group consisting of amines, phosphines, arsines and stibines in the presence of an epoxide, and
(3) a trivalent organophosphorus compound in the presence of an activated alkene or alkyne, said activated alkene or alkyne having the formula

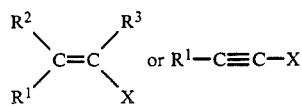

where X is an electron withdrawing group, and where R¹, R² and R³ are monovalent hydrocarbyl groups or hydrogen.

2. A process as claimed in claim 1 characterised in that the Lewis base containing catalyst is an amidine.

3. A process as claimed in claim 2 characterised in that the amidine is a guanidine.

4. A process as claimed in claim 2 characterised in that the amidine is a cyclic amidine.

5. A process as claimed in claim 4 characterised in that the cyclic amidine is a cyclic guanidine.

6. A process as claimed in claim 4 characterised in that the cyclic amindine has an amidine group which forms part of a fused ring system containing 6 and 5 membered rings, or 6 and 7 membered rings or two six membered rings.

7. A process as claimed in claim 6 characterised in that the cyclic amidine is selected from the group consisting of 1,5-diazabicyclo[4.3.0]non-5-ene, 1,8-diazabicyclo[5.4.0]undec-7-ene and 1,5,7-triazabicyclo[4.4.0]dec-5-ene.

8. A process as claimed in claim 1 characterised in that the Lewis base containing catalyst comprises a Lewis base and an epoxide.

9. A process as claimed in claim 8 characterised in that the Lewis base is an amine.

10. A process as claimed in claim 9 characterised in that the amine is an amidine.

11. A process as claimed in claim 9 characterised in that the amine is an alkylamine.

12. A process as claimed in claim 1 characterised in that the Lewis base containing catalyst comprises a trivalent organophosphorus compound in the presence of said activated alkene or alkyne.

13. A process as claimed in claim 12 characterised in that the trivalent organophosphorus compound is a mono-, di- or trialkyl phosphine or a mono-, di- or triaryl phosphine.

14. A process as claimed in claim 12 characterised in that the Lewis base catalyst is prepared by dissolving the trivalent organophosphorus compound and the activated alkene or alkyne in a solvent.

15. A process as claimed in claim 1 characterised in that X is an electron withdrawing group selected from —COOR, —COR, —CONH₂, CON(R)₂ or —CN where R is an alkyl or aryl group.

16. A process as claimed in claim 1 characterised in that the Lewis base containing catalyst is supported on an inert solid.

17. A process for the production of 1-methoxyethyl acetate characterised in that the process comprises reacting vinyl acetate with methanol in the presence of an effective amount of a Lewis base containing catalyst, said Lewis base containing catalyst comprising one or more of the following:
(1) an amidine,
(2) a Lewis base selected from the group consisting of amines, phosphines, arsines and stibines in the presence of an epoxide, and
(3) a trivalent organophosphorus compound in the presence of an activated alkene or alkyne, said activated alkene or alkyne having the formula

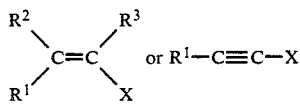

where X is an electron withdrawing group, and where R¹, R² and R³ are monovalent hydrocarbyl groups or hydrogen.

18. A process for the production of 1-ethoxyethyl acetate characterised in that the process comprises reacting vinyl acetate with ethanol in the presence of an effective amount of a Lewis base containing catalyst, said Lewis base containing catalyst comprising one or more of the following:
(1) an amidine,
(2) a Lewis base selected from the group consisting of amines, phosphines, arsines and stibines in the presence of an epoxide, and
(3) a trivalent organophosphorus compound in the presence of an activated alkene or alkyne, said activated alkene or alkyne having the formula

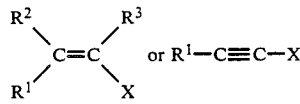

where X is an electron withdrawing group, and where R¹, R² and R³ are monovalent hydrocarbyl groups or hydrogen.

* * * * *

UNITED STATES PATENT AND TRADEMARK OFFICE
CERTIFICATE OF CORRECTION

PATENT NO. : 4,665,223

DATED : May 12, 1987

INVENTOR(S) : Michael James Green

It is certified that error appears in the above-identified patent and that said Letters Patent is hereby corrected as shown below:

Col. 1, line 19, "63" should read -- 63 --

Col. 1, lines 26 and 27, "via" and "48"
should read -- via -- and -- 48 --

Col. 3, line 44, "phosphate" should read -- phosphine --

Col. 4, line 58 "amberlite" should read -- Amberlite --

Col. 7, line 39, "amindine" should read -- amidine --

Signed and Sealed this

Third Day of November, 1987

*Attest:*

DONALD J. QUIGG

*Attesting Officer*  *Commissioner of Patents and Trademarks*